United States Patent [19]
Verbicky, Jr. et al.

[11] Patent Number: 4,471,125
[45] Date of Patent: Sep. 11, 1984

[54] METHOD FOR MAKING AROMATIC ETHER IMIDES

[75] Inventors: John W. Verbicky, Jr., Scotia, N.Y.; Brent A. Dellacoletta, Evansville, Ind.

[73] Assignee: General Electric Company, Schenectady, N.Y.

[21] Appl. No.: 426,387

[22] Filed: Sep. 29, 1982

[51] Int. Cl.$^3$ ............................................ C07D 209/48
[52] U.S. Cl. .................................. 548/476; 548/461; 548/481
[58] Field of Search ............... 548/461, 473, 476, 480, 548/481

[56] References Cited

U.S. PATENT DOCUMENTS 3,992,407 11/1976 Markezich .......................... 548/461
4,257,953 3/1981 Williams et al. .................... 548/461
4,273,712 6/1981 Williams ............................. 548/461

Primary Examiner—Donald G. Daus
Assistant Examiner—M. C. Eakin
Attorney, Agent, or Firm—William A. Teoli; James C. Davis, Jr.; James Magee, Jr.

[57] ABSTRACT

A method is provided for making aromatic ether imides in the substantial absence of a solvent. A mixture of at least one halo-substituted phthalimide and at least one anhydrous alkali metal phenoxide salt is heated at a temperature at least sufficient to convert the halo-substituted phthalimide to the molten state and below the temperature at which the alkali metal phenoxide is thermally unstable.

8 Claims, No Drawings

METHOD FOR MAKING AROMATIC ETHER IMIDES

CROSS REFERENCE TO RELATED APPLICATIONS

Reference is made to copending application Ser. No. 426,388 of John W. Verbicky, James A. Cella and Elbridge A. O'Neil, Jr., filed concurrently herewith and assigned to the same assignee as the present invention, herein incorporated by reference.

BACKGROUND OF THE INVENTION

The present invention relates to a method for making aromatic ether imides. More particularly, the present invention relates to the reaction of a halo-substituted phthalamide and anhydrous alkali metal phenoxide salt in the absence of an organic solvent and at a temperature at least sufficient to convert the halo-substituted phthalimide to the molten state.

Prior to the present invention, methods for making aromatic ether imides were generally based on the use of a dipolar aprotic solvent or non-polar aprotic solvent in conjunction with a phase transfer catalyst. For example, U.S. Pat. Nos. 3,879,428, 3,957,862 and 3,956,320, to Heath et al and U.S. Pat. No. 3,956,125 to Meyers form such compounds by condensation of an alkali metal phenoxide with a nuclear substituted phthalimide in the presence of a dipolar aprotic solvent. Additional methods for making aromatic ether imides are shown by Williams U.S. Pat. No. 4,273,712, Williams et al, U.S. Pat. No. 4,252,953 and Relles et al, U.S. Pat. No. 4,247,464, assigned to the same assignee as the present invention.

It would obviously be a substantial benefit to the art if aromatic ether imides could be formed without the necessity for using solvents which are expensive, require recycling and often require redistillation for reuse, in addition to leading to the possibility of chemical side reactions.

The present invention is based on the discovery that reaction can be effected between a halogen-substituted phthalimide of the formula,

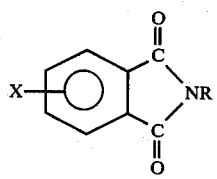

and an anhydrous alkali metal phenoxide salt of the formula,

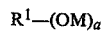

where R is a monovalent radical selected from hydrogen, a $C_{(1-8)}$ alkyl radical and a $C_{(6-13)}$ aryl radical, $R^1$ is a $C_{(6-30)}$ aromatic organic radical, X is chlorine, bromine or fluorine, preferably chlorine or bromine and most preferably chlorine, and M is an alkali metal ion, in the absence of an organic solvent by heating a mixture of these two components at a temperature in excess of the melting point of the halogen-substituted phthalimide. The use of a phase transfer catalyst has been found optional in the aforementioned reaction.

STATEMENT OF THE INVENTION

There is provided by the present invention a method for making aromatic ether imides of the formula,

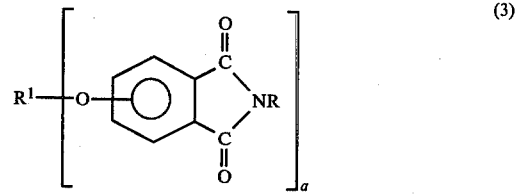

which comprises heating a mixture substantially free of organic solvent comprising halo-substituted phthalimide of formula (1) and anhydrous alkali metal phenoxide salt of formula (2), where the temperature of said mixture is at least sufficient to convert the halogen-substituted phthalimide to the molten state, where R and $R^1$ are as previously defined and a is an integer equal to 1 or 2, and when a is 1, $R^1$ is monovalent and when a is 2, $R^1$ is divalent.

The optional phase transfer catalyst used in the present invention can be represented by the formula:

$$(R^2)_4 QY \qquad (4)$$

wherein $R^2$ is a $C_{(1-16)}$ alkyl radical or a $C_{(6-13)}$ aromatic radical, Q is a Group Va element selected from N and P and Y is a halogen or a carbethoxy radical.

Radicals included by R, are for example, phenyl, tolyl, xylyl, naphthyl, chlorophenyl, bromonaphthyl, etc., and alkyl radicals such as methyl, ethyl, propyl, etc. Radicals included by $R^1$ are the aforementioned monovalent aromatic radicals included by R, divalent aromatic radicals, such as phenylene, tolylene, naphthylene, and $R^1$ more particularly includes

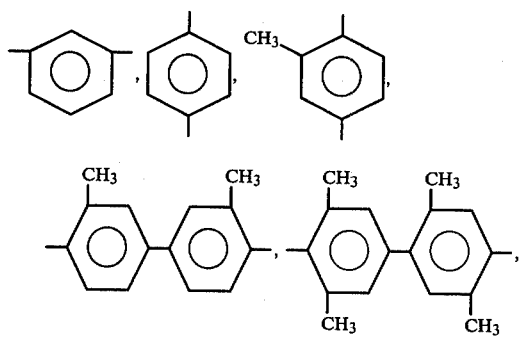

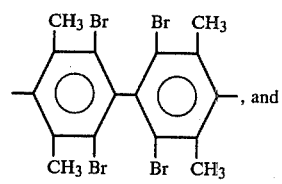

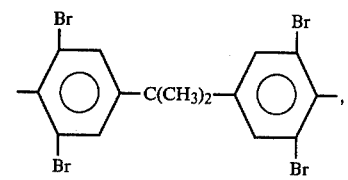

and divalent organic radicals of the general formula,

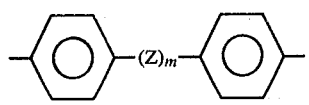

where Z is a member selected from the class consisting of divalent radicals of the formula,

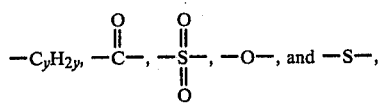

where m is 0 or 1, and y is a whole number from 1 to 5.

Radicals included by $R^2$ are, for example, propyl, butyl, pentyl, hexyl, heptyl, octyl and phenyl. M is more particularly sodium, potassium, lithium, rubidium, etc; Y is more particularly, chloro, bromo, iodo, acetato, etc.

Included within the halogen substituted phthalimides of formula (1) are, for example, 4-fluoro-N-methyl phthalimide, 3-fluoro-N-methyl phthalimide, 4-chloro-N-methyl phthalimide, 3-chloro-N-methyl phthalimide, etc.

Included within the phase transfer catalysts of formula (4) are, for example, tetrabutylammonium bromide, tetrapropylammonium bromide, tetrabutylammonium chloride, tetrabutylammonium fluoride, tetrabutylammonium acetate, tetrahexylammonium chloride, tetraheptylammonium chloride. Aliquat 336 phase transfer catalyst (methyltrioctylammonium chloride, manufactured by the General Mills Company), tetrabutylphosphonium bromide, tetraphenylphosphonium bromide, tetraphenylammonium bromide, tetrabutylphosphonium chloride, etc.

Some of the alkali metal salts of the above-described alkali phenoxides of formula (2) are sodium and potassium salt phenols, such as phenol, cresol, naphthol, etc; dihydric phenols, for example,
2,2-bis(2-hydroxyphenyl)propane;
2,4'-dihydroxydiphenylmethane;
bis(2-hydroxyphenyl)methane;
2,2-bis-(4-hydroxyphenyl)propane;
1,1-bis-(4-hydroxyphenyl)ethane;
1,1-bis-(4-hydroxyphenyl)propane;
2,2-bis-(4-hydroxyphenyl)pentane;
3,3-bis-(4-hydroxyphenyl)pentane;
4,4'-dihydroxybiphenyl;
4,4'-dihydroxy-3,3,5,5'-tetramethylbiphenyl;
2,4-dihydroxydiphenylsulfone;
4,4-dihydroxydiphenylsulfone;
2,4'-dihydroxydiphenylsulfone;
4,4'-dihydroxydiphenylsulfoxide;
4,4'-dihydroxydiphenylsulfide;
hydroquinone;
resorcinol;
3,4'-dihydroxydiphenylmethane;
4,4'-dihydroxybenzophenone; and
4,4'-dihydroxydiphenylether.

The halogen substituted phthalimides of formula (1) and the alkali metal phenoxide salts of formula (2) can be formed by the procedures outlined in U.S. Pat. No. 4,273,712, Williams, and U.S. Pat. No. 4,257,953, Williams et al, both hereby incorporated by reference.

If desired, mixtures of various alkali metal phenoxide salts, halogen substituted phthalimides and optional phase transfer catalysts can be used.

In accordance with the method of the present invention, it is preferred to effect reaction under substantially anhydrous conditions, although small amounts of moisture can be tolerated.

Temperatures at which reaction between the alkali metal phenoxide salt and the halogen substituted phthalamide can be effected range from above the melting point of the halogen substituted phthalimide to about 300° C., preferably from about 140° C. to about 300° C. and most preferably from 200° to 250° C.

The reaction system of the present invention must be fluid and, since the halogen substituted phthalimide is solid, the temperature must be sufficient to melt the same and provide a fluid system. The maximum temperature used in the method of the present invention is generally established by the fact that the thermal stability of the alkali metal phenoxide salt tends to lower at temperatures substantially in excess of 250° C.

The method of the present invention is generally practiced under an inert gas atmosphere, and while the nature of the inert gas used is not limited in any substantial fashion, typically nitrogen is used due to cost and availability. Argon, helium and the like could be used with equal success. Substantial amounts of oxygen should be excluded from the system.

Typically, reaction is at autogenous pressure, i.e., the reactor is filled at atmospheric pressure, closed, and the system heated to the temperature of reaction. Typically pressures on the order of 2000 psig are used, but pressure is relatively unimportant and is established, as will be appreciated by one skilled in the art, by the temperature of operation. Obviously, pressure should not be so high as to harm the reaction vessel.

The time of reaction is not overly important, and typically reaction is merely effected for a period of time sufficient to attain the desired aromatic ether imide without substantial amounts of starting materials being present which would require undue separation techniques. We have found four hours to be generally adequate to complete the reaction of the present invention though lesser and greater times can be used. While not to be construed as limitative in any fashion, we believe that commercial processing will involve times on the order of about 1 hour to about 8 hours.

One key aspect of the present invention is that the method of the present invention can be practiced without any substantial amount of solvent being present and, most preferably, is practiced without any solvent being present. Since no solvent is present, the earlier described disadvantages of solvent usage are avoided and the benefits of lower cost, lack of recycle, lack of distillation, and lack of competing side reactions due to solvent are achieved.

The ratio of the alkali meal phenoxide salt to halogen substituted phthalimide of the present invention is not overly important so long as sufficient halogen substituted phthalimide is present to provide a fluid system, which is necessary for the reaction to proceed. Essentially the halogen substituted phthalimide must be present in an amount sufficient to also function as a solvent in the present invention, i.e., it functions not only as a reactant with the alkali metal phenoxide salt but also as a solvent. So long as sufficient halogen substituted phthalimide is present to exhibit these two functions, the amounts are not overly limited.

We generally prefer to use at least about 20 moles of halogen substituted phthalimide to 1 mole of alkali metal phenoxide salt, but lesser amounts can be used so long as the two earlier described functions are exhibited. As will be apparent to one skilled in the art, greater amounts could be used, e.g., on the order of 50 moles halogen substituted phthalimide to 1 mole of alkali metal phenoxide salt, but as will also be apparent to one skilled in the art, recycle problems will be increased without any substantial benefit to the reaction system.

A phase transfer catalyst as earlier exemplified is optional per the present invention, albeit higher yields appear to be obtained if a phase transfer catalyst is used. A catalytic amount of the phase transfer catalyst is, of course, necessary to achieve increased yield. The amount can be freely selected, but generally is from about 0.005 molar equivalent to 2 molar equivalents of catalyst per molar equivalent of alkali metal phenoxide salt, more generally from about 0.02 to 0.05 equivalent same basis.

The aromatic ether imides of the present invention are recovered in a conventional fashion, for example, as disclosed in the Williams and Williams et al patents earlier incorporated by reference, e.g., cooling followed by recovery by filtration, precipitation in a precipitating solvent, for example, methanol, followed by standard recovery techniques such as filtration, extraction using a solvent such as methylene chloride, chloroform, etc., washing with water to effect removal of inorganic salts and the like.

If used, the phase transfer catalyst(s) and any by-products of the reaction can be recycled directly for further use.

The aromatic ether imides of the present invention can be used to form engineering thermoplastics following the procedure of U.S. Pat. Nos. 3,879,428 and 3,847,867, hereby incorporated by reference.

The following examples are given by way of illustration and not by way of limitation. All parts are by weight unless otherwise indicated and all mixtures were agitated, for example, using a stirrer. Unless otherwise indicated, all materials used were reagent grade.

EXAMPLE 1

A mixture of 0.440 g (3.80 mmol) of anhydrous sodium phenoxide and 1.50 g (76.7 mmol) of 4-chloro-N-methyl phthalimide is heated to 250° C. for 4 hours under a nitrogen gas atmosphere in an autoclave. There was obtained a 45.6% yield of 4-phenoxy-N-methyl phthalimide based on the phenoxide as determined by gas or liquid chromatographic analysis using o-terphenyl as an internal standard. The product was identified by a comparison of its retention time with that of an authentic sample of the desired material in a conventional matter.

The above reaction is repeated, except that the product is recovered from the autoclave in conventional manner and the excess 4-chloro-N-methyl phthalimide is distilled from the resulting autoclave reaction product at a temperature of 294°-295° C., at a pressure of 720 torr. The resulting product is then extracted with toluene and then filtered to effect removal of insoluble salts. There is obtained 4-phenoxy-N-methyl phthalimide at substantially the same yield as indicated above.

EXAMPLE 2

Example 1 was repeated except that 1.0 mole % of 15-crown-5, a phase transfer catalyst having the formula,

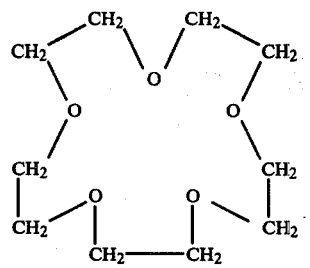

was added to the reaction mixture based on the alkali metal phenoxide salt. There was obtained about a 63% yield of the 4-phenoxy-N-methyl phthalimide in about the same period of time.

Although the above examples are directed to only a few of the very many variables which can be utilized in the practice of the method of the present invention, it should be understood that the present invention is directed to the use of a much broader variety of halo-substituted phthalimide of formula (1) and alkali metal phenoxide salt of formula (2) and to the resulting aromatic ether imide produced therefrom of formula (3).

What we claim as new and desire to secure by Letters Patent of the United States is:

1. A method for making aromatic ether imides of the formula,

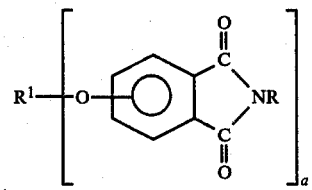

which comprises heating a mixture substantially free of organic solvent comprising halo-substituted phthalimide of the formula

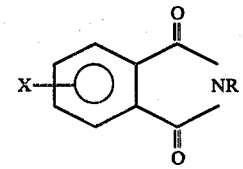

and anhydrous alkali metal phenoxide salt of the formula

$R^1$—(OM)$_a$ where the temperature of said mixture is at least sufficient to convert the halogen-substituted phthalimide to the molten state, where R is a monovalent group selected from hydrogen, a $C_{(1-8)}$ alkyl group, a $C_{(6-13)}$ aryl group and a $C_{(6-13)}$ halogenated aryl group, $R^1$ is a $C_{(6-30)}$ monovalent or divalent aromatic organic group selected from the class consisting of

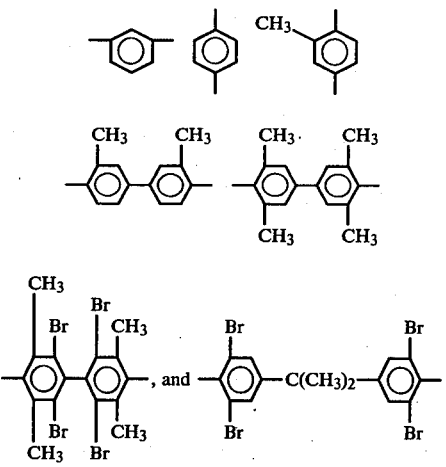

and divalent organic groups of the general formula,

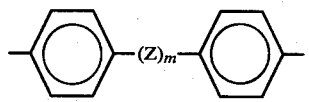

where Z is a member selected from the class consisting of divalent group of the formula,

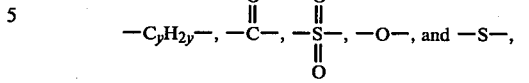

where m is 0 or 1, and y is a whole number from 1 to 5, X is selected from chlorine, bromine or fluorine, M is an alkali metal ion, a is an integer equal to 1 to 2, and when a is 1, $R^1$ is monovalent and when a is 2, $R^1$ is divalent.

2. The method of claim 1 wherein X is chlorine.

3. The method of claim 1 wherein X is bromine.

4. The method of claim 1 wherein the heating is at from about 140° C. to about 300° C.

5. The method of claim 1 wherein the heating is at from about 200° C. to about 250° C.

6. The method of claim 1 wherein said reaction is conducted at autogenous pressure under an inert gas atmosphere.

7. The method of claim 1 wherein said reaction is conducted in the complete absence of solvent other than the halogen substituted phthalimide.

8. The method of claim 1 wherein said reaction is conducted in the presence of a catalytically effective amount of a phase transfer catalyst.

* * * * *